(12) United States Patent
Largeaud

(10) Patent No.: US 8,123,040 B2
(45) Date of Patent: Feb. 28, 2012

(54) DEVICE FOR CHARACTERIZING THE PARTICLE SIZE DISTRIBUTION OF POWDERS AND ITS USES

(75) Inventor: Gil Largeaud, Clamant (FR)

(73) Assignee: Omya S.A.S., Paris (FR)

( * ) Notice: Subject to any disclaimer, the term of this patent is extended or adjusted under 35 U.S.C. 154(b) by 35 days.

(21) Appl. No.: 12/310,741

(22) PCT Filed: Sep. 12, 2007

(86) PCT No.: PCT/IB2007/002644
§ 371 (c)(1),
(2), (4) Date: Mar. 5, 2009

(87) PCT Pub. No.: WO2008/032192
PCT Pub. Date: Mar. 20, 2008

(65) Prior Publication Data
US 2009/0281654 A1    Nov. 12, 2009

(30) Foreign Application Priority Data
Sep. 14, 2006 (FR) ...................... 06 08038

(51) Int. Cl.
*B07B 9/00* (2006.01)
(52) U.S. Cl. ....... 209/44.3; 209/288; 209/291; 209/546; 209/659
(58) Field of Classification Search ............... 209/44.3, 209/288, 291, 659
See application file for complete search history.

(56) References Cited

U.S. PATENT DOCUMENTS

| | | | | |
|---|---|---|---|---|
| 2,537,159 A | * | 1/1951 | Sallander | 74/26 |
| 3,486,427 A | * | 12/1969 | Waschulewski et al. | 404/117 |
| 3,749,372 A | * | 7/1973 | Funk | 366/60 |
| 4,184,944 A | | 1/1980 | Tytko | |
| 4,282,090 A | * | 8/1981 | Hoernschemeyer et al. | 209/291 |
| 4,487,323 A | * | 12/1984 | Marrs | 209/546 |
| 6,829,955 B1 | * | 12/2004 | Mahgerefteh | 73/865.5 |
| 2009/0281654 A1 | * | 11/2009 | Largeaud | 700/223 |

FOREIGN PATENT DOCUMENTS

| | | |
|---|---|---|
| FR | 2 275 117 A | 1/1976 |
| WO | WO 84/04473 | 11/1984 |
| WO | WO 2006/123037 A | 11/2006 |

OTHER PUBLICATIONS

"PCT International Search Report" for PCT Application No. PCT/IB2007/002644, as published under WO 2008/032192 A2 on Mar. 20, 2008 (8 pages).
Written Opinion for PCT Application No. PCT/IB2007/002644.

* cited by examiner

*Primary Examiner* — Terrell Matthews
(74) *Attorney, Agent, or Firm* — Amster, Rothstein & Ebenstein LLP

(57) ABSTRACT

The invention is a device for characterizing the particle size distribution of powders, comprising a supply member, a discharge member, a weighing member, a continuous vibration member, a screening member and, optionally, a control member, said device being characterized in that the screening member is a member that rotates about a horizontal axis and has at least four positions corresponding to two screens of different mesh size, one release space and one anti-shock plate. Another subject of the invention is the use of such a device for characterization of the particle size distribution of powders and especially their in-line characterization, that is to say characterization during their manufacturing process.

30 Claims, 6 Drawing Sheets

DEVICE FOR CHARACTERIZING THE PARTICLE SIZE DISTRIBUTION OF POWDERS AND ITS USES

This is a U.S. national phase of PCT Application No. PCT/IB2007/002644, filed Sep.12, 2007, which claims priority to French Application No. 0608038, filed Sep.14, 2006.

The invention relates to the sector of devices and apparatuses for determining the particle size distribution of powders, said characterisation particularly being able to be performed in-line, i.e. during the manufacturing process of said powders.

The powders concerned are more specifically dry powders, i.e. powders having a moisture content less than 5% by weight of water, as determined by means of differential weighing measurements before and after drying of said powders.

The powders concerned are also powders having a wide particularly size distribution range, i.e. wherein the mean diameter is between 0.05 and 10 mm.

The powders concerned are more specifically powders used in the food sector, such as powders based on sugar crystals, salt powders, flours, powdered milk, powders consisting of dehydrated food materials, washing powders, ceramic powders, plastic powders, metallic powders, paint powders, pharmaceutical powders, printing toner, fertilisers, or powders consisting of mineral materials, and more specifically mineral material powders based on natural and/or precipitated calcium carbonate and/or dolomites and/or talc, and more specifically mineral material powders based on a natural calcium carbonate which is marble, chalk, limestone or mixtures thereof.

Figure 1:
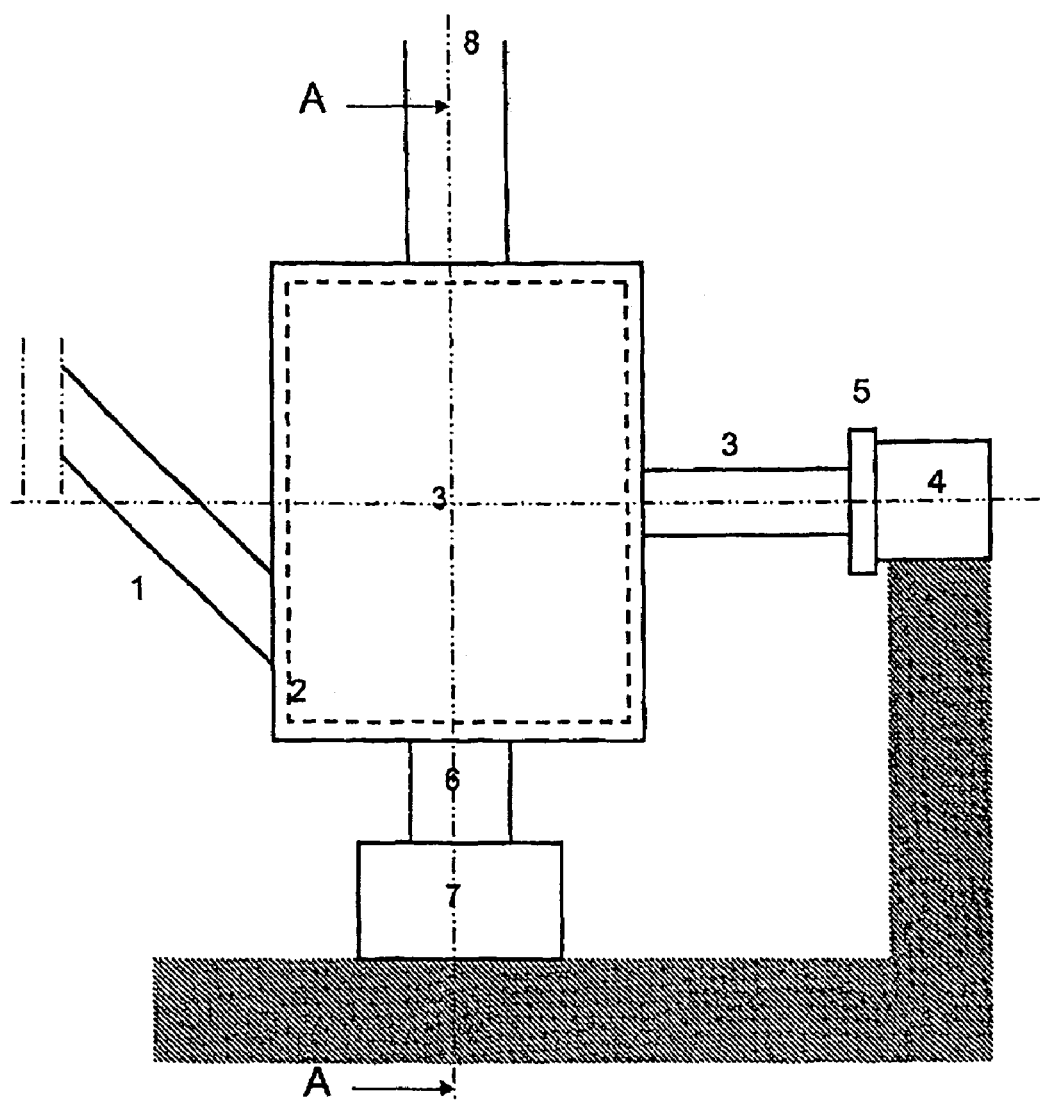
FIG. 1 (denoted as FIG. 1/6) represents a schematic front view of the device according to the present invention.

A first aim of the invention is a device for characterising the particle size distribution of powders, comprising a supply member, a discharge member, a weighing member, a continuous vibration member, a screening member and, optionally, a control member, and characterised:

in that the screening member is a member that rotates about a horizontal axis and has at least one position for an empty space or powder release and introduction space, one position for an anti-shock plate, at least two positions corresponding to two positions of different mesh size;

and in that said device has a cleaning member consisting of at least one nozzle and/or one ultrasound generator located at the periphery of the screening member;

and in that said device has a resilient coupling member between the horizontal axis of the screening member and the continuous vibration member.

Another aim of the invention is the use of such a device for characterisation of the particle size distribution of powders, and especially their in-line characterisation, i.e. characterisation during their manufacturing process.

It particularly relates to dry powders, i.e. powders wherein the moisture content is less than 5% by weight of water, as determined by means of differential weighing measurements before and after drying of said powder.

It also relates to powders having a wide particle size distribution range, i.e. wherein the mean diameter is between 0.05 and 10 mm.

Finally, it relates to powders used in the food sector, such as powders based on sugar crystals, salt powders, flours, powdered milk, powders consisting of dehydrated food materials, washing powders, ceramic powders, plastic powders, metallic powders, paint powders, pharmaceutical powders, printing toner, fertilisers, or powders consisting of mineral materials, and more specifically mineral material powders based on natural and/or precipitated calcium carbonate and/or dolomites and/or talc, and more specifically mineral material powders based on a natural calcium carbonate which is marble, chalk, limestone or mixtures thereof.

A first aim of the invention is a device for characterising, optionally in-line, the particle size distribution of various powders, such as in particular the dry powders as defined above, having a wide particle size distribution also as defined above, and particularly the different categories of powders as defined in the previous paragraph.

The term in-line particle size distribution characterisation is used by the Applicant to refer to the monitoring of the particle size distribution of the manufacturing process of said powders, and particularly during the particle size reduction process of said powders in the case of powders consisting of mineral materials.

Another aim of the invention is to provide a device for characterising different particle size classes for the above-mentioned powders simultaneously.

Another aim of the invention lies in the fact that the device produced in this way is simple to implement on a production site of said powders, and compatible with the industrial constraints of such a site.

Another aim of the invention is to offer a device for characterising the particle size distribution of said powders during the manufacturing process thereof, without altering said powders or altering said device: in this way, the integrity of the particulate material under analysis is maintained and the durability of the device over time is ensured.

Another aim of the invention is to perform the cleaning of said device automatically (without any operation by an operator) which helps both reduce maintenance costs and maintain the integrity of the device and the results thereof.

A final aim of the invention is to provide a device for characterising the particle size distribution of said powders where the weighing system is not altered by the vibrations from the continuous vibration member.

It should be noted that the latter three aims (preservation of powders and devices, automatic cleaning, freedom from vibrations) are necessarily met for the present invention in that the features helping achieve these aims are obligatory and not optional. This represents a fundamental distinction with respect to French patent No. 05 04917.

In the field of powders, the monitoring of the particle size distribution thereof is a fundamental element for those skilled in that art, general engineers in industrial processes specialised in powdery material techniques. Indeed, this monitoring makes it possible to assess the quality of the manufactured product during the different particle size reduction steps for mineral material powders. In the more general field of dry powders, particularly mineral material powders, plastic, metallic, ceramic or washing powders, and sugars, such monitoring also enables those skilled in the art to ensure the efficiency of the manufacturing process, while guaranteeing precise specifications in terms of fineness and particle size for the end customer.

In the field of sugar, it is indeed well known that the size distribution of individual crystals influences the dissolution in water of the sugar lump formed by said crystals, as described in "Dissolution of sugar" (Zuckerindustrie Berlin 1990, 115 (4), pp 250-60).

The same applies for washing tablets wherein the solubility in water is among other times governed by the size distribution of the constituent individual particles, said factor also influencing the pourability of said powders, as described in the document "Production of a granulated laundry detergent using pneumatic nozzle" (Inzyniera i Aparatura Chemiczna (1996), 35 (3), pp 15-18).

In the field of ceramics, it is also well known that the particle size distribution of a calcium carbonate powder may have an influence on the pourability properties of said powder, or on the drying of ceramic materials containing said powder, as specified in "Influence of mean particle size on drying-shrinkage behaviour of calcium carbonate slip cast bodies"(Proceedings of the China International Conference on High-Performance Ceramics, $1^{st}$, Beijing, China, Oct. 31-Nov. 3, 1998 (1999), Meeting Date 1998, pp 181-184).

In the sector of powders used in plastic industries, it is also well known that this particle size distribution plays a very important role in the pourability of said powders. The same applies for metallic powders.

Finally, in the mineral industry, it is well known that this particle size distribution of powders is a primordial factor liable to influence numerous properties of the end product containing said powders, particularly based on calcium carbonate. Indeed, numerous works link this particle size distribution with the dissolution of calcium carbonate ("Dissolution kinetics of $CaCO_3$ in powder form and influence of particle size and pretreatment on the course of dissolution", Industrial & Engineering Chemistry Research (1996), 35 (2), pp 465-74), the mechanical properties of plastic formulations containing calcium carbonate ("Effect of $CaCO_3$ particle size grading on rheological property of polypropylene", Feijinshukuang (2001), 24 (2), pp 13-14), the optical properties of sheets of paper manufactured with coating slips containing calcium carbonate ("Effect which the particle size of ground calcium carbonate exerts on color rheology and coated paper rheology", Kami Pa Gikyoshi (1999), 53 (9), pp 1174-1178), or the structure of paint films containing calcium carbonate ("The influence of particle size distribution of natural calcium carbonate on the structure of a paint film using mercury porosimetry", Double Liaison—Chimie des Peintures (1986), 33(372), pp 25-37, VII-XVIII).

With a view to monitoring the particle size distribution of said powders, particularly in the mineral industry, those skilled in the art must therefore have a device that is:
  easy to install in the manufacturing process and simple to use,
  usable in-line in the particle size reduction process of said mineral materials (in order to monitor the fineness thereof at a given point of said process—typically at the outlet of a grinding and/or selection device),
  compatible with the industrial constraints of a production site (such as vibrations associated with the use of grinders, the inherent shocks from the movement of various items of equipment, an atmosphere frequently charged with powdery particles, etc.).

With a view to characterising the particle size distribution of various powders, it is well known, at the very last on a laboratory scale, to use techniques such as Transmission, Diffusion Electron Microscopy, methods based on gas adsorption, optical means based on X-ray diffraction, conventional Optical Microscopy, or laser technologies. In this way, the document "Comparison of various particle sizing techniques" (Journal of Wuhan University of Technology, Materials Science Edition, 2000, 15 (2), pp 7-14) describes the use of these techniques for measuring the characteristic dimensions of aluminium oxide powders in the field of ceramics.

As examples of commercial apparatuses that can be used to determine the particle size distribution of powders, and using some of the techniques mentioned above, the Applicant may cite the Mastersizer™ laboratory laser granulometer range manufactured by Malvern™, the Insitec™ in-line laser granulometer range manufactured by the same company, and Sedigraph™ type devices manufactured by Micromeritics wherein the technology is based on X-ray diffraction.

In this way, in the fields concerned by the present invention, the document "Alcoholic crystallisation of sucrose" (Thesis, University of Queensland, Department of chemical engineering, 1E0406/7, 2000) reports on the use of a Mastersizer™ granulometer for determining the size of sugar crystals. This apparatus was used successfully for determining the particle size distribution of plastics, as described in "Physical properties and compact analysis of commonly used direct compression binders" (AAPS PharmSciTech. 2003, 4(4), article 62). Similarly, "Colloidal processing of hydroxyapatite" (Biomaterials, 22, 2001, pp 1847-1852) describes the implementation of a Sedigraph™ 5100 type device, for determining the particle size distribution of hydroxyapatite powders used in the manufacture of ceramic materials.

It is also known to use in the general field of powders, particle size distribution measurement devices based on analysis of images taken using cameras. Those skilled in the art know in this field apparatuses under the brand Camsizer™ marketed by Retsch Technology™, CAP™ marketed by Haver and Boecker™, or Part An™ marketed by Norske Hydro™.

However, such devices involve a number of drawbacks. Their particle size measurement range is, depending on the devices, narrow. These devices are specialised on a measurement range. They cannot simultaneously measure on a range from a few dozen microns to several millimeters. Using techniques such as lasers, cameras, etc., the results are deduced from statistical calculations: they require adjustment by means of correlations which are long to process. The statistical method does not make it possible to give the section of the product, which is essential for the quality of the delivered product. In addition, these precision apparatuses are poorly adapted to the inherent vibrations of the presence of some items of equipment, such as grinders frequently encountered in the mineral industry. These vibrations also disturb devices wherein the particle size measurement range is wider, such as image analysis optical systems, which, due to the insufficient field depth, do not make it possible to obtain a necessary and sufficient image quality for characterising the abovementioned powders except using micrometric image focussing technologies, that cannot be used in an industrial environment such to constraints (vibrations, etc.). In addition, numerous devices are relatively costly; they are based on techniques requiring frequently long and thorough development of the samples under analysis, under strict cleanliness conditions which are sometimes difficult to obtain in the case of a mineral material manufacturing unit (existence of powdery materials in the atmosphere). Moreover, some technologies only make it possible to characterise very small quantities of powder (a few grams), which poses the problem of the representative nature of the samples with respect to the actual production capacities of the majority of industrial tools. Finally, these measurement devices, per se, should undergo numerous modifications in order to be used at a specific point of the manufacturing process, to perform the in-line particle size distribution measurement of the powders manufactured, which represents the primary requirement for those skilled in the art.

Also, those skilled in the art prefer to opt for characterisation apparatuses based on a selection of particles according to the size thereof, using mechanical devices, based either on sieves, screens and meshes, or on springs. The Applicant will now review the documents accessible to those skilled in the art in each of these two categories.

The category of devices based on sieves, screens and networks is extremely wide. As such, the Applicant specifies that the international patent classification ($8^{th}$ edition) class B07B relating to sieving, screening, sifting, or sorting solid materials using networks, gratings, grids, or the like comprises on the date of filing of the present Application more than 17,789 documents.

Of these, it is possible to distinguish devices based on rotating and/or vibrating screens, having different geometries. In this way, the document U.S. Pat. No. 4,184,944 describes a cylindrical screen device, rotating continuously about the horizontal axis thereof, and making it possible to screen dry or wet powders through the screen covering said cylinder. In parallel, the document EP 1 163 958 describes a cylindrical apparatus rotating continuously on the horizontal axis thereof, said horizontal movement being completed by a vibration movement induced on the screen which forms the cylinder: this device is specifically intended for screening clay-based materials.

As a general rule, the Applicant specifies that the use of cylindrical cages covered with a screen, actuated by a rotation and/or vibration movement, thus enabling the screening of mineral particles, are means well known to those skilled in the art. Moreover, in addition to the abovementioned devices, it is common to perform weighing of materials screened in this way, which makes it possible to obtain a mass proportion of particles wherein the diameter is less than the mesh size of the screen used. However, these devices are not satisfactory for those skilled in the art as they are used industrially to separate materials of different types and/or wash materials polluted by particles of very different sizes. Therefore, they are not intended for characterising powders. These devices are, in addition, equipped with a single type of screen covering the entire circumference thereof, optionally making it possible to only characterise a single particle size class. Furthermore, none of these devices disclose systems making it possible to measure the particle size distribution of powders in-line.

In the category of apparatuses based on sieves, screens or other gratings, the Applicant is finally aware of the document U.S. Pat. No. 4,487,323 which describes a device for characterising the particle size distribution of powders, based on a drum rotating about the horizontal axis thereof having an opening and various screens. The drum adopts different positions about the axis thereof and is shaken by a vibrating motor, which enables the screening of the powder contained therein through the screen which is facing downwards. Scales located under the drum, and detached from the assembly, make it possible to quantify the mass of particles having passed through each screen. However, such a device does not enable the in-line characterisation of the particle size distribution of powder as the operator must add the powder to be tested in the drum by hand.

In addition, those skilled in the art turn to the category of powder particle size distribution measurement devices, particularly using springs.

In fact, this technology appears to be much more recent than that mentioned above (based on gratings, screens or sieves). For this reason, the number of documents contained therein is much lower, and it is easier for those skilled in the art to rapidly identify devices enabling them to possibly solve the problem of characterising the particle size distribution of different powders in-line, during the manufacturing process thereof.

In this way, those skilled in the art rapidly identify the recent document U.S. Pat. No. 6,829,955 B1 (U.S. patent published on 14 Dec. 2004). This document describes a device for determining the particle size distribution, in-line, and in a relatively simple manner, of various powders. Such a device is equipped with a spring wherein the spacing of the turns, which is variable according to the oscillation amplitude of said spring, will make it possible to allow different particle size classes to pass. However, such a device may also pose new problems to those skilled in the art, although it makes it possible to characterise the particle size distribution of various powders in line. Indeed, as specified in the figure of the cover page of said document, the particles of powder under analysis, when they fall in the reception chamber located above the spring are the source of a dual drawback: the energy thereof may be sufficiently high so that they are altered at the time of impact with the spring (the integrity of the material under test is no longer ensured) and/or they alter the spring by damaging the turns or by modifying the spacing thereof (the integrity of the device and therefore of the measurement is no longer ensured).

Also, with a view to solving the initial technical problem, consisting of the development of a device for the in-line characterisation of the particle size distribution of powders, that is simple to install in industry, compatible with industrial constraints such as vibrations, the Applicant has developed a device which, while fulfilling these conditions, remedies the drawbacks relating to the document U.S. Pat. No. 6,829,955 which represents the closest prior art as it already solves the initial technical problem, these drawbacks being the alteration of the material under analysis and the degradation of the measurement device.

The development of the device according to the invention appears to involve an inventive step as it is no way based on the document representing the closest prior art, that those skilled in that should have tried to improve in an obvious and natural manner.

On the contrary, very inventively, the Applicant succeeded in identifying a much older document, U.S. Pat. No. 4,487,323, from a very extensive set of documents as it concerns that consisting of apparatuses based on sieves, screens or gratings (17,789 documents as of 8 May 2006 in international patent classification class B07B), wherein it widely transformed the functioning, to solve the technical problem.

The choice of this document was less natural/obvious for those skilled in the art as said document U.S. Pat. No. 4,487, 323 does not solve, as already mentioned above, the initial technical problem stated in the present Application. Indeed, the Applicant wishes to point out that the in-line characterisation of the particle size distribution of powders cannot be performed using the device described in the document U.S. Pat. No. 4,487,323. Indeed, several human interventions are required in said document, with a view to characterising the particle size distribution of a powder: introduction of same into the screening drum, with in particular the risk of the screens being damaged (and therefore manual replacement of the screens) or clogged (and therefore manual cleaning of the screens) during the introduction thereof, and/or of the powder being altered when it comes into contact with the screens (and therefore discharging of the powder, manual cleaning of the screens, and new introduction of the powder to repeat the measurement), cleaning/general maintenance of the devices, particularly of the screens. Conversely, the device according to the present invention does not require any manual intervention during the screening cycle (also without damaging/clogging the screens or altering the powder), or for cleaning the screens. In addition, it is equipped with a supply member which makes it possible to collect the powder under analysis directly in the manufacturing process thereof (sampling on a hopper or in a silo, for example): in this way, said device may be perfectly synchronised with the very manufacturing process of said powder.

After identifying this document, the Applicant succeeded in modifying the device according to same to:
  solve the initial technical problem (i.e. enable the determination of the particle size distribution of powders, in-line, simply, in a manner compatible with industrial constraints such as vibrations);
  while solving said initial technical problem, avoid the drawbacks associated with the alteration of the material under test and the degradation of the device, which are detected in the document U.S. Pat. No. 6,829,955;

Therefore, with a view to solving the initial technical problem, i.e. enabling the in-line determination of the particle size distribution of powders simply, in a manner compatible with industrial constraints, the Applicant introduced a supply member making it possible to introduce the powders under test directly in the horizontal screening member, which was not included in document U.S. Pat. No. 4,487,323. However, such a choice would inevitably result in the sudden arrival of the powder under analysis on the screen, potentially altering said powder and/or damaging the screens: in this way, the problems involved in the document U.S. Pat. No. 6,829,955 were encountered, which demonstrates that this choice was not natural. One of the merits of the Applicant lies in the manner in which it solved this drawback: it equipped the horizontal screening member with an anti-shock plate which was not included in the document U.S. Pat. No. 4,487,323, said plate having an anti-shock feature being positioned downwards at the start of the measurement cycle, to receive the powder under test. In this way, the screens are no longer damaged and the powder under test is no longer altered, which guarantees the integrity of both. The anti-shock plate is in fact a stainless steel frame equipped with a pad made using a natural rubber (good abrasion resistance) and a silicone gel. The gel is characterised in that it prevents any bouncing of the product by absorbing the energy of the shock without returning it.

In this way, those skilled in the art have, by means of the present invention, a device for characterising powders in-line that is simple to implement, compatible with the vibrations found in an industrial production unit, which does not degrade the powder under analysis and which is not altered in contact with said powder: this represented the primary requirement for those skilled in the art.

Finally, there are two other secondary advantages offered by the present invention, and which were not offered by the document U.S. Pat. No. 4,487,323. The Applicant underlines that these two other advantages are not associated with another technical problem, as they may be associated with the initial technical problem, as described above. The Applicant has simply chosen to present them as secondary technical problems, in that the solutions thereof only represent optional features of the present invention.

The first is that the device described in the document U.S. Pat. No. 4,487,323 is not easy to implement in that the measurement member is detached from the rest of the apparatus: if it is necessary to move the device, it is therefore necessary to move the measurement member, which requires a dual handling procedure. However, attaching the measurement member to the rest of the device will render it dependent on the vibrations induced by the continuous vibration member, and therefore incapable of providing a reliable measurement. Another merit of the Applicant lies in this case in the solution implemented which consists of actually attaching the measurement member to the rest of the device, but also consists of providing a resilient coupling member between the motor and the horizontal axis of the screening member. In this way, this combination makes it possible to provide a one-piece device (does not require multiple procedures for moving in the factory) and wherein the service life of the vibration member is increased. Indeed, the Applicant noted that, the vibration system making it possible to vibrate the rotating cage by vibrating the axis coupled therewith, breaking the axis/motor connection by means of a resilient coupling member made it possible to prevent the transmission of vibrations on the motor: therefore, the service life thereof is thus increased. Said resilient coupling member, well known to those skilled in the art, may particularly be an elastomer type member.

The second is associated with the simple implementation requirement and relates to the cleaning of the device. The merit of the Applicant lies in this case in that it succeeded in noting that an automatic cleaning member, consisting of at least one nozzle and/or an ultrasound generator located at the periphery of the screening member and spraying compressed air on the screens would make it possible, in combination with one or more rotations of said screens, to clean the entire device completely and perfectly, in a very short time interval.

Finally, the Applicant wishes to specify that it is aware in the prior art of French Patent No. 05 04917, and which only falls within the scope of the prior in terms of novelty (according to article L611-14 of the French Intellectual Property Code, or according to article 54(2) of the European Patent Convention). However, there is, among other things, a fundamental difference between said Application and the present invention, in that, in the four positions of the rotating member, wherein one is an anti-shock plate, in the case of the present invention.

Also, a first aim of the invention is a device for characterising the particle size distribution of powders, comprising a supply member, a discharge member, a weighing member, a continuous vibration member, a screening member and, optionally, a control member, and characterised:
  in that the screening member is a member that rotates about a horizontal axis and has at least one position for an empty space or powder release and introduction space, one position for an anti-shock plate, at least two positions corresponding to two positions of different mesh size;

and in that said device has a cleaning member consisting of at least one nozzle and/or one ultrasound generator located at the periphery of the screening member;

and in that said device has a resilient coupling member between the horizontal axis of the screening member and the continuous vibration member.

FIG. 1 represents a very schematic front view of the device according to the present invention, the hatched part representing the frame whereon the device according to the present invention is attached, so as to provide cohesion between the various members of said device.

Therefore, said device is equipped with a supply member 1 whereby the powder under analysis enters the screening member 2. Those skilled in that will be able to adapt the supply member so as to connect it to a silo, a hopper, or any other point of the manufacturing process of the powder under test, so as to perform at said point sampling of said powder, with a view to bringing it into the device according to the invention. In this way, it is possible to carry out the in-line determination of the particle size distribution of the powders under test, which is one of the advantages of the present invention.

Figure 2:
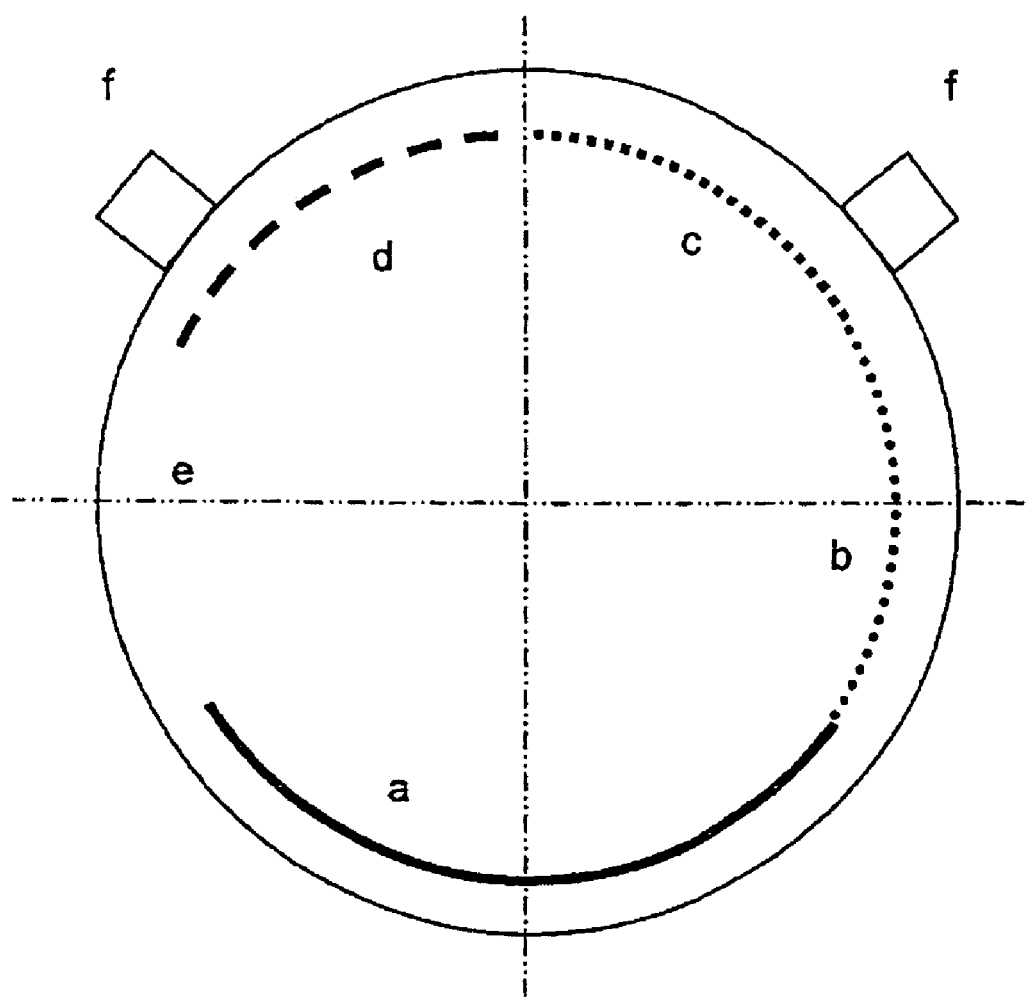
FIG. 2 (denoted as FIG. 2/6) illustrates the cylindrical screen member as observed along an AA section of FIG. 1.

The screening device is a rotating member about the horizontal axis thereof 3 and in this figure, the free space, the various screens or the anti-shock plate belonging to the features of said screening member have not been represented (refer to FIG. 2, detailed above). The continuous vibration member 4 communicates the vibrations thereof to the axis 3 which transmits them to the screening member. The resilient coupling member 5 limits the propagation of the vibrations from the screening member to the continuous vibration member: the service life of said continuous vibration member is thus increased.

In this way, this gives a one-piece device that is simple to implement and particularly to move in a plant, and wherein the service life of the continuous vibration member is extended: this represents one of the other advantages of the present invention.

The various particle size classes of the particles under analysis flow off through the screens of the screening member, via the discharge member 6 and the weight thereof is finally quantified on the weighing member 7.

FIG. 2 illustrates schematically the cylindrical screening member, as may particularly be observed along an AA section of FIG. 1.

During the powder characterisation cycle, the screening member is arranged such that the anti-shock plate a is positioned downwards. In this way, the powder under test arrives directly onto said plate a via the opening e: the materials are not altered (they do not break particularly in contact with the rigid screens, as in the case of the prior art) and they do not damage said screens either (as in the case of the prior art): the integrity of the powder under analysis is thus preserved along with the integrity of the measurement device and particularly the screens. This is the main advantage offered by the present invention.

Indeed, said device preserves the integrity of the powders under analysis, and cannot be damaged by said powders. With respect to maintaining the integrity of the material under analysis, the Applicant wishes to point out that this is an essential requirement so as not to vitiate the weighing measurement. However (this is a further ancillary advantage of the present invention), the fact that the powder reaches the anti-shock plate without being damaged, optionally makes it possible to perform on said powder present on the plate another non-destructive measurement such as, for example and without wishing to be limitative, an optical measurement, such as a particularly important colour measurement in the case of a mineral material such as calcium carbonate. In addition, the present device does not comprise the disadvantages of the laboratory methods mentioned above, as it is inexpensive to manufacture, simple to integrate and use and the conditions of the implementation thereof are perfectly compatible with the industrial environment wherein it is used (atmosphere rich in powdery materials, shocks, vibrations, etc.). Then, unlike other mechanical devices according to the prior art, it makes it possible to simultaneously (without changing screens or interrupting the measurement cycle) characterise several particle size classes. Finally, the simplicity thereof renders it perfectly suitable at any point of the mineral material manufacturing process, thus enabling in-line monitoring of the particle size distribution of said particles, which is the essential aim for those skilled in the art.

The characterisation cycle may then start. Once all the powder under analysis has been introduced automatically onto the anti-shock plate, the screening member is rotated until the screen with the finest mesh size b, located exactly next to the anti-shock plate, is in the downward position: a first powder particle size class is thus screened. The operation is repeated for the screen c located exactly next to the screen b and which has a larger mesh size than said screen, and for screen d located exactly next to the screen c and which has a larger mesh size than said screen. Finally, after a final rotation, the rotating member is positioned such that the empty space is positioned downwards: the particles remaining in the cylinder are therefore discharged downwards, and are weighed on the scales.

Therefore, this figure represents the device according to the invention equipped with 3 different mesh sizes (b, c and d); this number is not limitative, and it is noted that the device according to the present invention must comprise at least 2 different mesh sizes. The device is designed to handle several positions and therefore several screens suitable for the monitoring of the manufacturing process of the powder under analysis.

In this way, due to the successive positions adopted by the screening member about the horizontal axis thereof, the particles are brought onto screens of increasingly large mesh sizes: the particles are thus classified according to the size thereof. The weighing system associated with the device makes it possible to measure the particle masses wherein the diameter is less than the mesh size of each of the screens: this gives, by referencing each particle mass as a function of the total weight of the sample, a particle size distribution of the particles. The results obtained may be expressed in "fines" (Percentage of particles passing through the screens), "residue" (percentage of particles remaining in the screens, i.e. the opposite of "fines") or according to any other means of expression of this type of results.

At the end of the characterisation cycle of the sample taken, said sample is returned to the manufacturing cycle during an automatic cleaning operation according to the invention (so-called "backflush" operation). The purpose of this cleaning step is to discharge the powder found in the weighing member, clean the screens of the screening member, remove the dust from the overall device and reset the apparatus (original position for start-ups and/or initialisations following a possible failure of the invention, or starting standby position of a new cycle during the use of the invention).

It consists of:
opening the weighing member to discharge the sample,
rotating the screening member on one or more revolutions,
spraying compressed air on the rotation screens, particularly via nozzles located on either side of the screening member, as represented in FIG. 2, f, or projecting ultrasound via generators located on either side of the screening member, sucking in the dust raised by the compressed air, the initial positioning of the device.

The dust raised by the compressed air may then be sucked in by a low pressure system (8 in FIG. 1), found on all industrial powder manufacturing sites.

Otherwise, the system may easily be equipped with an autonomous low pressure system.

The number of screens, the particle passage time on each, the total mass of the particles introduced initially in the screening member are all parameters that those skilled in the art will be able to adapt to the type of powders to be characterised.

In addition to the distribution of the particles according to the particle size thereof, the invention makes it possible, during a simplified cycle using only the screen having the largest mesh size and the release position of the coarsest particles, to identify possible pollution of the powder analysed by particles of excessively large diameters, which should not be present in said powder. These particles of excessively large diameter are generally present in small quantities, hence the need to use a simplified cycle, enabling the sampling of a sample of significant mass compared to the mass of the sample analysed during the complete cycle.

Also, a first aim of the invention is a device for characterising the particle size distribution of powders, comprising a supply member, a discharge member, a weighing member, a continuous vibration member, a screening member and, optionally, a control member, and characterised:

in that the screening member is a member that rotates about a horizontal axis and has at least one position for an empty space or powder release and introduction space, one position for an anti-shock plate, at least two positions corresponding to two positions of different mesh size;

and in that said device has a cleaning member consisting of at least one nozzle and/or one ultrasound generator located at the periphery of the screening member;

and in that said device has a resilient coupling member between the horizontal axis of the screening member and the continuous vibration member.

The supply, discharge, weighing and continuous vibration members may be produced according to any shape and any means well known to those skilled in the art.

The same applies for the screening member, provided that it is rotating about a horizontal axis, and comprises at least four positions corresponding to two different mesh sizes, one empty coarsest particle powder introduction and release space and one anti-shock plate.

The device is also characterised in that the anti-shock plate is made of stainless steel and is equipped with a pad produced using natural rubber and silicone gel.

The device is also characterised in that the resilient coupling member is of the elastomer type.

The device according to the invention is also characterised in that the screening member is produced in different shapes, particularly cylindrical or polygonal.

Therefore, the device according to the invention may optionally comprise a control member, wherein the function is to control the other members. Said control member may be onboard or remote. It may consist of a computer, a PLC, or any other control member well known to those skilled in the art.

A further aim of the invention is the use of the device described above for determining the particle size distribution of powders.

The use of the device according to the invention is also characterised in that it enables the determination of the particle size distribution of powders by means of the different successive positions adopted by the screening member about the horizontal axis thereof, the initial position of the screening member consisting of the anti-shock plate positioned downwards.

This use is also characterised in that the determination of the particle size distribution of the powders takes place in-line, i.e. during the manufacturing process thereof.

This use is characterised in that said powders are dry powders, i.e. powders wherein the moisture content is less than 5% by mass of water, and preferentially less than 2% by mass of water, and very preferentially less than 1% by mass of water, as determined by differential weighings, before and after drying of said powder.

This use is also characterised in that said powders have a particle size distribution range, such that the mean diameter of said powders is between 0.05 and 10 mm, preferentially between 0.1 and 5 mm, very preferentially between 0.2 and 2 mm.

This use is also characterised in that said powders are powders used in the food sector, such as powders based on sugar crystals, salt powders, flours, powdered milk, powders consisting of dehydrated food materials, washing powders, ceramic powders, plastic powders, metallic powders, paint powders, pharmaceutical powders, printing toner, fertilisers, or powders consisting of mineral materials, and more specifically mineral material powders based on natural and/or precipitated calcium carbonate and/or dolomites and/or talc, and more specifically mineral material powders based on a natural calcium carbonate which is marble, chalk, limestone or mixtures thereof.

The examples below illustrate the invention without limiting the scope thereof.

EXAMPLES

Example 1

This example illustrates the implementation of the invention for the characterisation of the particle size distribution of a powder which is calcium carbonate manufactured by OMYA™ in its plant in Salse (France) and subsequently marketed under the brand Durcal™ 130.

For this purpose, the device according to the invention was equipped with four screens wherein the mesh sizes are equal to 100 µm, 250 µm, 355 µm and 500 µm, meeting the analytical requirements of said powder (customer quality specifications, etc.). The passage times of the powder on each of the screens are respectively equal to 06:00 minutes, 07:30 minutes, 04:00 minutes, 00:30 minutes and finally 00:25 minutes on the coarsest particle release position.

The corresponding results, expressed as a percentage of particles wherein the diameter is greater than the mesh size of each screen (referred to as the residue) are given in table 1.

TABLE 1 residue at 100 μm, 250 μm, 355 μm and 500 μm,
determined using the device according to the invention, on a dry
calcium carbonate powder (Durcal ™ 130 marketed by OMYA ™).

| Residue at 100 μm (%) | Residue at 250 μm (%) | Residue at 355 μm (%) | Residue at 500 μm (%) |
|---|---|---|---|
| 82.09 | 30.55 | 0.55 | 0 |
| 78.76 | 29.39 | 0.39 | 0 |
| 79.35 | 28.47 | 0.29 | 0 |
| 81.15 | 29.54 | 0.39 | 0 |
| 81.06 | 30.21 | 0.19 | 0 |
| 78.37 | 27.16 | 0.3 | 0 |
| 79.82 | 27.63 | 0.1 | 0 |

Therefore, table 1 demonstrates that it is possible, using the device according to the invention, to obtain the particle size distribution of a powder such as calcium carbonate.

Example 2

The aim of this invention is to demonstrate the reliability of the device according to the invention, by illustrating the correlation between the measurements made, and the measurements made manually in the laboratory on the same samples.

This example uses a powder which is calcium carbonate manufactured by OMYA™ in its plant in Salse (France) and subsequently marketed under the brand Durcal™ 130.

Different samples of said powder were analysed by the device according to the invention, under the same conditions as those described for example 1.

In parallel, these samples were screened manually, via a 100 μm screen and another 250 μm screen.

Figure 3:
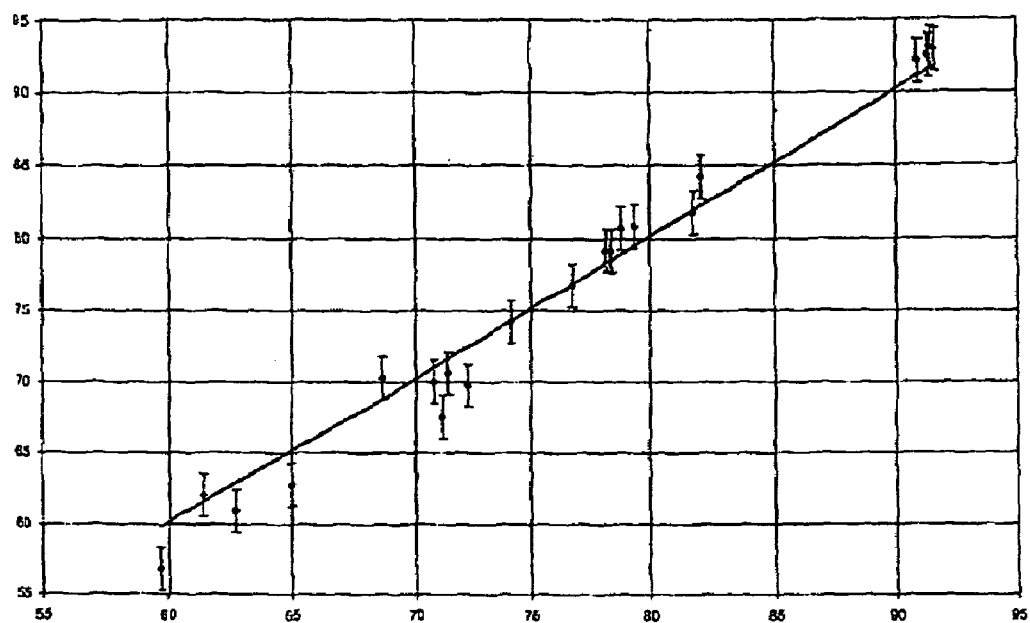
FIG. 3 (denoted as FIG. 3/6) represents the residue value measured according to the manual laboratory test (Y-axis) as a function of the residue measured according to the invention (X-axis) at 100 µm.
Figure 4:
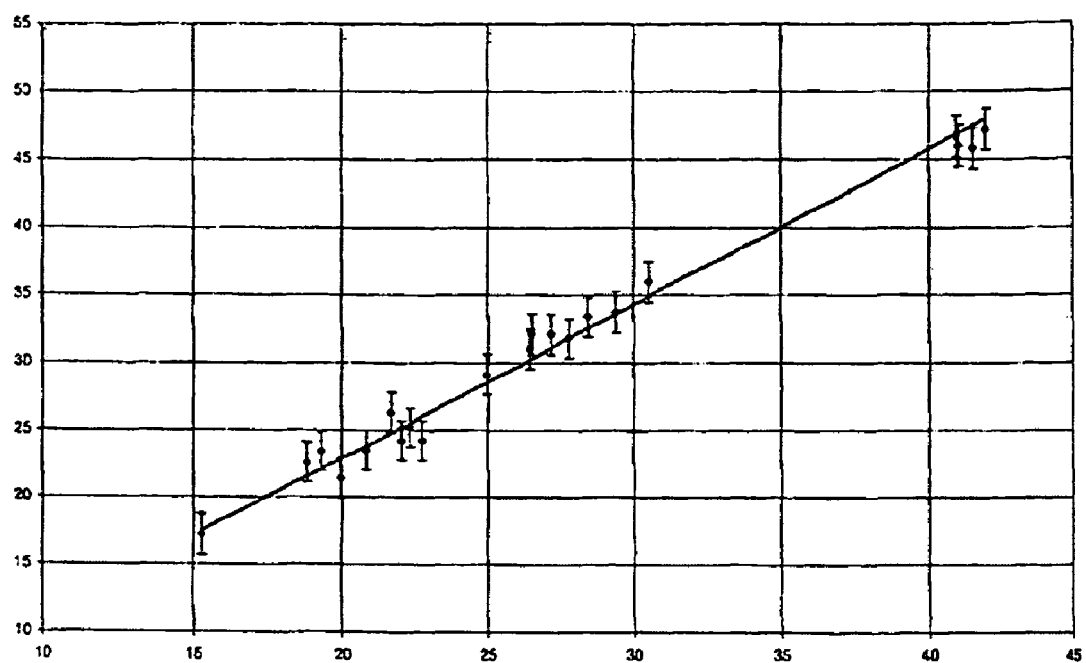
FIG. 4 (denoted as FIG. 4/6) represents the residue value measured according to the manual laboratory test (Y-axis) as a function of the residue measured according to the invention (X-axis) at 250 µm.

FIGS. 3 and 4, at the end of this document, represent the residue value measured according to the manual laboratory test (axis of the ordinate or Y-axis) as a function of the residue measured according to the invention (axis of abscissas or X-axis) respectively:

- at 100 μm (FIG. 3 wherein the linear regression line having the equation y=1.0018x and having a regression coefficient equal to 0.9751 is represented)
- and at 250 μm (FIG. 4 wherein the linear regression line having the equation y=1.1437x and having a regression coefficient equal to 0.9856 is represented).

The reading of FIGS. 3 and 4 demonstrates the excellent correlation between the measurements made manually at 100 and 250 μm, and those obtained directly by means of the device according to the invention on the same samples (this correlation is naturally possible for products other than Durcal™ 130 and for other particle size distribution points such as 63 μm, 80 μm, 355 μm, etc.).

Example 3

This example illustrates the implementation of the invention for the characterisation of the particle size distribution of a powder which is crystal sugar in the form of powder manufactured by Cristal Union™ in its plant in Corbeilles (France) and subsequently in the form of powdered sugar.

For this purpose, the device according to the invention was equipped with five screens wherein the mesh sizes are equal to 125 μm, 250 μm, 500 μm, 630 μm and 800 μm, meeting the analytical requirements of said powder (customer quality specifications, etc.). The passage times of the powder on each of the screens are respectively equal to 06:30 minutes, 06:00 minutes, 06:00 minutes, 05:00 minutes, 03:30 minutes and finally 02:30 minutes on the coarsest particle release position.

The corresponding results, expressed as a percentage of particles wherein the diameter is greater than the mesh size of each screen (referred to as the residue) are given in table 2.

TABLE 2 residue at 125 μm, 250 μm, 500 μm, 630 μm and 800 μm,
determined using the device according to the invention, on a dry
crystal sugar powder (marketed by CRISTAL UNION ™).

| Residue at 125 μm (%) | Residue at 250 μm (%) | Residue at 500 μm (%) | Residue at 630 μm (%) | Residue at 800 μm (%) |
|---|---|---|---|---|
| 98.4 | 94.5 | 60.7 | 37.6 | 18.1 |
| 98.7 | 93.3 | 57.4 | 38.2 | 19.5 |
| 99.1 | 93.9 | 55.5 | 38.7 | 18.6 |
| 98.8 | 94.4 | 59.5 | 41.3 | 20.5 |
| 99.4 | 93.7 | 56.9 | 40.2 | 17.8 |
| 98.5 | 93.4 | 57.3 | 39.8 | 19.4 |

Therefore, table 2 demonstrates that it is possible, using the device according to the invention, to obtain the particle size distribution of a powder such as sugar.

Example 4

The aim of this invention is to demonstrate the reliability of the device according to the invention, by illustrating the correlation between the measurements made, and the measurements made manually in the laboratory on the same samples.

This example uses a powder which is crystal sugar manufactured by CRISTAL UNION™ in its plant in Corbeilles (France) and subsequently marketed under the brand Candy™.

Different samples of said powder were analysed by the device according to the invention, under the same conditions as those described for example 3.

In parallel, these samples were screened manually, via a 250 μm screen and another 630 μm screen.

Figure 5:
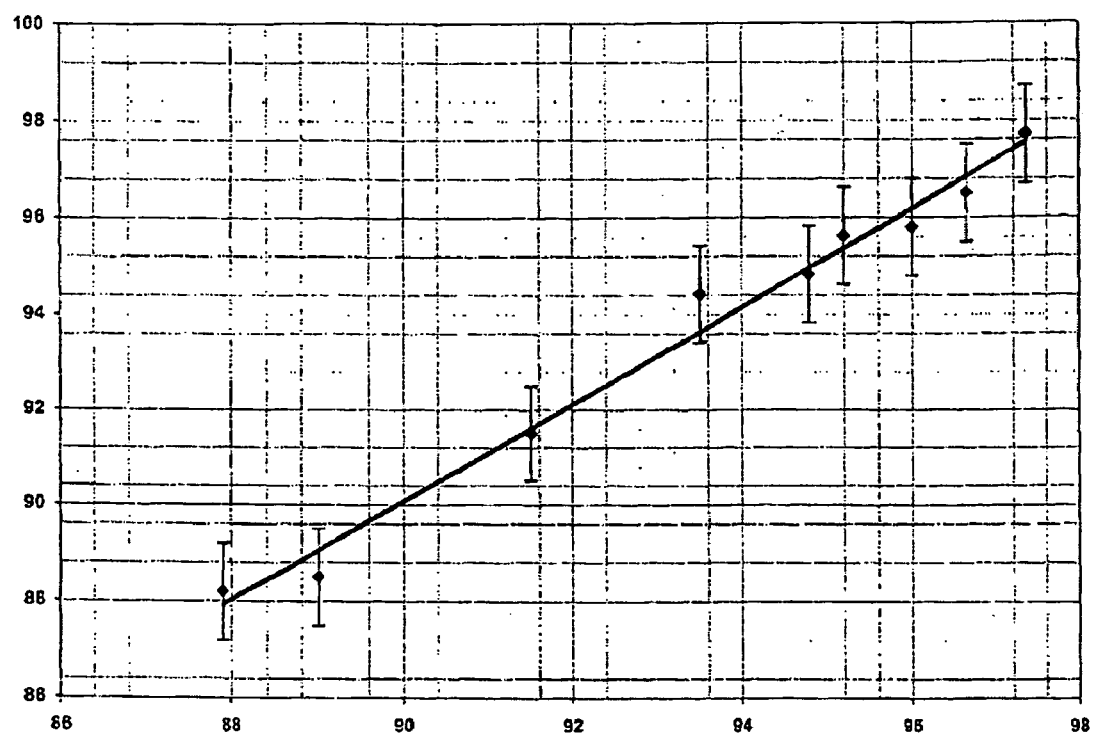
FIG. 5 (denoted as FIG. 5/6) represents the residue value measured according to the manual laboratory test (Y-axis) as a function of the residue measured according to the invention (X-axis) at 250 µm.
Figure 6:
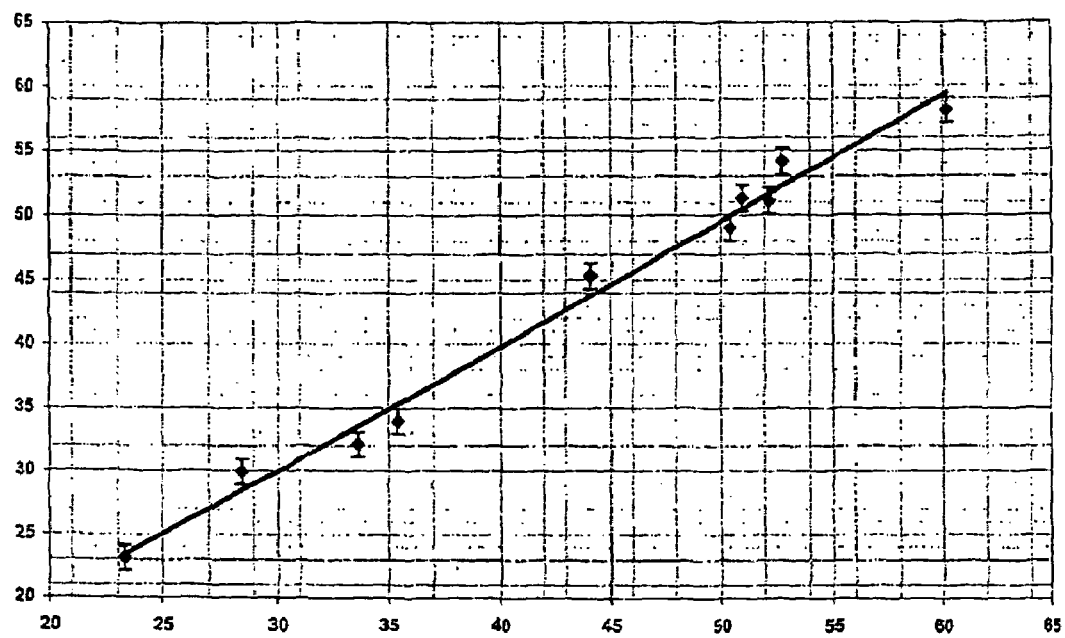
FIG. 6 (denoted as FIG. 6/6) represents the residue value measured according to the manual laboratory test (Y-axis) as a function of the residue measured according to the invention (X-axis) at 630 µm.

FIGS. 5 and 6, at the end of this document, represent the residue value measured according to the manual laboratory test (axis of the ordinate or Y-axis) as a function of the residue measured according to the invention (axis of abscissas or X-axis) respectively:

- at 250 μm (FIG. 5 wherein the linear regression line having the equation y=1.0175x−1.51 and having a regression coefficient equal to 0.986 is represented)
- and at 630 μm (FIG. 6 wherein the linear regression line having the equation y=0.9773x−0.6 and having a regression coefficient equal to 0.988 is represented).

The reading of FIGS. 5 and 6 demonstrates the excellent correlation between the measurements made manually at 250 and 630 μm, and those obtained directly by means of the device according to the invention on the same samples (this correlation is naturally possible for different types of crystal sugar and for other particle size distribution points such as 125 μm, 500 μm, 800 μm, etc.).

The invention claimed is:

1. A device for characterising the particle size distribution of powders, comprising a supply member, a discharge member, a weighing member, a continuous vibration member, a screening member and, optionally, a control member, wherein the screening member is a member that rotates about a horizontal axis and has at least one position for an empty space or powder release and introduction space, one position for an anti-shock plate having a shock absorbing pad for receiving powder, and at least two positions corresponding to two positions of different mesh size for screening powder, wherein the device has a cleaning member comprising at least one nozzle and/or one ultrasound generator located at the periphery of the screening member, wherein the device has a resilient coupling member between the horizontal axis of the screening member and the continuous vibration member, and wherein the anti-shock plate is not a screen.

2. The device according to claim 1, wherein the screening member is cylindrical or polygonal in shape.

3. The device according to claim 1, wherein the anti-shock plate is made of stainless steel and is equipped with a pad produced using natural rubber and silicone gel.

4. The device according to claim 1, wherein the resilient coupling member is of the elastomer type.

5. The device according to claim 1, comprising a control member.

6. The device according to claim 1, wherein the anti-shock plate of the screening member is positioned downwards.

7. The device according to claim 5, wherein the control member is an onboard or remote control member.

8. The device according to claim 5, wherein the control member is a computer or a PLC.

9. A method for determining the particle size distribution of a powder comprising introducing the powder into the device of claim 1, and determining the particle size distribution of the powder.

10. The method according to claim 9, wherein the determination of the particle size distribution of the powder takes place in-line during the manufacturing of the powder.

11. The method according to claim 9, wherein the powder has a moisture content of less than 5% by mass of water, as determined by differential weighings, before and after drying of the powder.

12. The method according to claim 9, wherein the powder has a moisture content of less than 2% by mass of water, as determined by differential weighings, before and after drying of the powder.

13. The method according to claim 9, wherein the powder has a moisture content of less than 1% by mass of water, as determined by differential weighings, before and after drying of the powder.

14. The method according to claim 9, wherein the powder has a mean diameter of between 0.05 and 10 mm.

15. The method according to claim 9, wherein the powder has a mean diameter of between 0.1 and 5 mm.

16. The method according to claim 9, wherein the powder has a mean diameter of between 0.2 and 2 mm.

17. The method according to claim 9, wherein the powder is used in the food sector.

18. The method according to claim 17, wherein the powder comprises sugar crystals, salt, flour, powdered milk or dehydrated food material.

19. The method according to claim 9, wherein the powder is a washing powder.

20. The method according to claim 9, wherein the powder is a ceramic powder.

21. The method according to claim 9, wherein the powder is a plastic powder.

22. The method according to claim 9, wherein the powder is a metallic powder.

23. The method according to claim 9, wherein the powder is a paint powder.

24. The method according to claim 9, wherein the powder is a pharmaceutical powder.

25. The method according to claim 9, wherein the powder is a printing toner.

26. The method according to claim 9, wherein the powder is a fertilizer.

27. The method according to claim 9, wherein the powder is a mineral matter.

28. The method according to claim 9, wherein the powder comprises natural and/or precipitated calcium carbonate and/or dolomites and/or talc.

29. The method according to claim 9, wherein the powder comprises natural calcium carbonate.

30. The method according to claim 29, wherein the calcium carbonate is prepared from marble, chalk, limestone or mixtures thereof.

* * * * *